(12) United States Patent
Uram

(10) Patent No.: US 10,226,167 B2
(45) Date of Patent: Mar. 12, 2019

(54) LASER VIDEO ENDOSCOPE

(75) Inventor: Martin Uram, Little Silver, NJ (US)

(73) Assignee: Beaver-Visitec International, Inc., Waltham, MA (US)

( * ) Notice: Subject to any disclaimer, the term of this patent is extended or adjusted under 35 U.S.C. 154(b) by 0 days.

(21) Appl. No.: 13/314,371

(22) Filed: Dec. 8, 2011

(65) Prior Publication Data

US 2012/0078042 A1    Mar. 29, 2012

Related U.S. Application Data

(63) Continuation-in-part of application No. 12/779,214, filed on May 13, 2010.

(51) Int. Cl.
*A61B 1/04* (2006.01)
*G02B 23/24* (2006.01)
*G02B 23/26* (2006.01)
*A61B 1/00* (2006.01)

(52) U.S. Cl.
CPC ............ *A61B 1/042* (2013.01); *A61B 1/0017* (2013.01); *G02B 23/2484* (2013.01); *G02B 23/26* (2013.01); *A61B 1/0011* (2013.01)

(58) Field of Classification Search
None
See application file for complete search history.

(56) References Cited

U.S. PATENT DOCUMENTS

| | | |
|---|---|---|
| 3,941,121 A | 3/1976 | Olinger et al. |
| 4,537,193 A | 8/1985 | Tanner |
| 4,607,622 A | 8/1986 | Fritch et al. |
| 4,671,273 A | 6/1987 | Lindsey |
| 4,702,245 A | 10/1987 | Schroder et al. |
| 4,754,328 A | 6/1988 | Barath et al. |
| 4,807,594 A | 2/1989 | Chatenever |
| 4,837,857 A | 6/1989 | Scheller et al. |

(Continued)

FOREIGN PATENT DOCUMENTS

| | | |
|---|---|---|
| DE | 19542955 A1 | 5/1997 |
| EP | 0512592 A1 | 11/1992 |

(Continued)

OTHER PUBLICATIONS

International Search Report and Written Opinion of PCT/US2011/034464.

(Continued)

*Primary Examiner* — Alexandra L Newton
(74) *Attorney, Agent, or Firm* — Budzyn IP Law, LLC

(57) ABSTRACT

A laser video endoscope has a laser guide, an illumination guide and an image guide. These are fiber optical guides which extend through the optical probe and through a hand piece that supports the probe. The hand piece is connected by a first relatively long flexible optical fiber cable to a laser energy source and a source of illumination. By contrast, the image is transmitted from the hand piece to an image presentation site by a camera assembly that is mounted to the hand piece and a relatively long electrical cable. The camera and its electrical cable can be uncoupled from the hand piece and used in a plurality of endoscopic routines. The rest of the product, including the probe and the hand piece, can be disposed of after each medical routine thereby providing assurance of an antiseptic procedure.

7 Claims, 7 Drawing Sheets

(56) References Cited

U.S. PATENT DOCUMENTS

| | | | | |
|---|---|---|---|---|
| 5,121,740 | A * | 6/1992 | Uram | 600/108 |
| 5,323,766 | A | 6/1994 | Uram | |
| 5,409,480 | A | 4/1995 | Uram | |
| 5,419,312 | A | 5/1995 | Arenberg et al. | |
| 5,643,250 | A | 7/1997 | O'Donnell, Jr. | |
| 5,738,676 | A | 4/1998 | Hammer et al. | |
| 5,788,628 | A | 8/1998 | Matsuno et al. | |
| 5,807,242 | A | 9/1998 | Scheller et al. | |
| 5,865,831 | A | 2/1999 | Cozean et al. | |
| 5,868,665 | A * | 2/1999 | Biggs | 600/112 |
| 5,893,828 | A | 4/1999 | Uram | |
| 5,983,749 | A | 11/1999 | Holtorf | |
| 6,080,101 | A | 6/2000 | Tatsuno et al. | |
| 6,179,829 | B1 | 1/2001 | Bisch et al. | |
| 6,193,650 | B1 | 2/2001 | Ryan, Jr. | |
| 6,260,434 | B1 | 7/2001 | Holtorf | |
| 6,355,027 | B1 | 3/2002 | Le et al. | |
| 6,360,630 | B2 | 3/2002 | Holtorf | |
| 6,368,269 | B1 | 4/2002 | Lane | |
| 6,419,627 | B1 | 7/2002 | Ben Nun | |
| 6,451,005 | B1 | 9/2002 | Saitou et al. | |
| 6,452,123 | B1 | 9/2002 | Chen | |
| 6,572,536 | B1 | 6/2003 | Bon et al. | |
| 6,639,332 | B2 | 10/2003 | Metzler et al. | |
| 6,689,975 | B2 | 2/2004 | Metzler et al. | |
| 6,862,951 | B2 | 3/2005 | Peterson et al. | |
| 6,997,868 | B1 | 2/2006 | Uram | |
| 7,012,203 | B2 | 3/2006 | Hanson et al. | |
| 7,189,226 | B2 | 3/2007 | Auld et al. | |
| 7,289,139 | B2 | 10/2007 | Amling et al. | |
| 7,435,218 | B2 | 10/2008 | Krattiger et al. | |
| 7,439,463 | B2 | 10/2008 | Brenner et al. | |
| 7,470,277 | B2 | 12/2008 | Finlay et al. | |
| 7,522,797 | B2 * | 4/2009 | Treado et al. | 385/117 |
| 7,626,132 | B2 | 12/2009 | Mezhinsky | |
| 7,781,941 | B2 | 8/2010 | Horvath et al. | |
| 7,845,537 | B2 | 12/2010 | Shelton, IV et al. | |
| 7,846,150 | B2 | 12/2010 | Hamel et al. | |
| 7,942,814 | B2 | 5/2011 | Remijan et al. | |
| 7,972,326 | B2 | 7/2011 | Scheller | |
| 8,029,499 | B2 | 10/2011 | Zimare et al. | |
| 8,038,602 | B2 | 10/2011 | Gill et al. | |
| 8,048,094 | B2 | 11/2011 | Finlay et al. | |
| 8,159,370 | B2 | 4/2012 | Shields et al. | |
| 8,194,122 | B2 | 6/2012 | Amling et al. | |
| 8,323,181 | B2 | 12/2012 | Mukherjee | |
| 8,348,924 | B2 | 1/2013 | Christian et al. | |
| 8,545,396 | B2 | 10/2013 | Cover et al. | |
| 8,599,250 | B2 | 12/2013 | Amling et al. | |
| 8,647,333 | B2 | 2/2014 | Mansour | |
| 8,680,412 | B2 | 3/2014 | Horvath et al. | |
| 8,749,188 | B2 | 6/2014 | Tran et al. | |
| 2003/0036680 | A1 | 2/2003 | Black | |
| 2003/0083552 | A1 | 5/2003 | Remijan et al. | |
| 2005/0033309 | A1 | 2/2005 | Ryan | |
| 2005/0113641 | A1 | 5/2005 | Bala | |
| 2005/0143626 | A1 | 6/2005 | Prescott | |
| 2005/0192480 | A1 * | 9/2005 | Toriya et al. | 600/182 |
| 2006/0025655 | A1 | 2/2006 | Uram | |
| 2006/0084952 | A1 | 4/2006 | Pallikaris et al. | |
| 2006/0276690 | A1 * | 12/2006 | Farris et al. | 600/162 |
| 2007/0135806 | A1 | 6/2007 | Easley | |
| 2007/0139924 | A1 | 6/2007 | Easley et al. | |
| 2007/0139950 | A1 | 6/2007 | Easley et al. | |
| 2007/0166662 | A1 | 7/2007 | Lint et al. | |
| 2007/0213586 | A1 | 9/2007 | Hirose et al. | |
| 2007/0293727 | A1 * | 12/2007 | Goldfarb et al. | 600/178 |
| 2008/0071143 | A1 | 3/2008 | Gattani et al. | |
| 2008/0114387 | A1 | 5/2008 | Hertweck et al. | |
| 2008/0140158 | A1 | 6/2008 | Hamel et al. | |
| 2008/0150754 | A1 | 6/2008 | Quendt | |
| 2009/0259098 | A1 * | 10/2009 | Krattiger | 600/109 |
| 2010/0198200 | A1 | 8/2010 | Horvath | |
| 2010/0204609 | A1 | 8/2010 | Worth et al. | |
| 2010/0318074 | A1 | 12/2010 | Dacquay et al. | |
| 2011/0282139 | A1 | 11/2011 | Uram | |
| 2012/0083800 | A1 | 4/2012 | Andersohn | |
| 2012/0191078 | A1 | 7/2012 | Yadlowsky et al. | |
| 2012/0203075 | A1 | 8/2012 | Horvath et al. | |
| 2012/0215065 | A1 | 8/2012 | Mukherjee | |
| 2012/0265010 | A1 | 10/2012 | Uram | |
| 2013/0324794 | A1 | 12/2013 | Cover et al. | |
| 2014/0066723 | A1 | 3/2014 | Horvath et al. | |
| 2014/0121653 | A1 | 5/2014 | Abe et al. | |
| 2016/0095507 | A1 | 4/2016 | Uram et al. | |

FOREIGN PATENT DOCUMENTS

| | | |
|---|---|---|
| JP | 6470023 A | 3/1989 |
| JP | H05115501 A | 5/1993 |
| JP | 6-80401 | 11/1994 |
| JP | 2001-218851 A | 8/2001 |
| JP | 2004-16317 A | 1/2004 |
| JP | 2005237436 A | 9/2005 |
| JP | 2005-532139 A | 10/2005 |
| JP | 2006-223710 A | 8/2006 |
| WO | 9849929 A1 | 11/1998 |
| WO | 2008/108425 A1 | 12/2008 |
| WO | 2010143402 A1 | 12/2010 |

OTHER PUBLICATIONS

The above patent documents were cited in a Supplementary European Search Report dated Mar. 5, 2014, that issued in the corresponding European Patent Application No. 11781025.9.

* cited by examiner

LASER VIDEO ENDOSCOPE

CROSS REFERENCE TO RELATED APPLICATION

This application is a continuation-in-part of U.S. patent application Ser. No. 12/779,214 filed on May 13, 2010, the entire disclosure of which is hereby incorporated by reference.

BACKGROUND OF THE INVENTION

This invention relates in general to a medical laser video endoscope and more particularly to one in which the operating probe may be economically disposed of after each use.

Laser video endoscopes are known and in particular are described in Applicant's issued U.S. Pat. No. 5,121,740 issued on Jun. 16, 1992 and U.S. Pat. No. 6,997,868 issued on Feb. 14, 2006. The disclosures of those two patents are incorporated herein by reference.

The endoscopes such as the ones described in those two patents, are reused after autoclaving or other sterilization. Reuse occurs in large part because of the expense of the endoscope. The most significant expense factor is the image guide which has a large number of micron size optical fibers. In one endoscope 17,000 fibers were employed thereby providing a 17,000 pixel image.

The image guide currently used costs about $200.00. This is a major incentive for the use of the endoscope after sterilization rather than disposing of the endoscope after each procedure.

This expense factor means that as a practical matter the endoscope will be reused after sterilization rather than disposed of.

However, there is greater security from infection if the probe of the endoscope can be disposed of after each usage instead of being subject to the possibilities of human error in the sterilization process.

Accordingly, it is a key purpose of this invention to provide an endoscope design for which the cost is reasonable enough to permit and encourage disposal of the probe after each use rather then have recourse to sterilization.

It is a related purpose of this invention to provide this cost improvement in a design that maintains a probe design with which the surgeon is familiar and which also maintains the rest of the operating characteristics of the known laser video endoscopes.

It is a further aspect of this invention to provide a laser video endoscope which is less costly than are the current designs.

BRIEF DESCRIPTION

A laser video endoscope has a laser guide, an illumination guide and an image guide. These are fiber optical guides which extend through the optical probe and through a hand piece that supports the probe. The illumination guide and laser guide extend through a first channel of the hand piece to and through a relatively long flexible optical fiber cable to a laser energy source and a source of illumination. The optical image guide extends through a second channel of the hand piece. The proximal end of the image guide is at the proximal end of the second channel. A camera assembly is connected to the proximal end of the hand piece, at the end of the second channel, and is optically coupled to the end of the optical fiber image guide. A relatively long electrical cable transmits an electrical image signal from the camera assembly to a site where an image can be provided for the surgery.

The camera and its electrical cable can be uncoupled from the hand piece and reused in a plurality of endoscopic routines.

The rest of the product including the probe and the hand piece can be disposed of after each medical routine thereby providing assurance of an antiseptic procedure.

BRIEF DESCRIPTION OF THE DRAWINGS

FIG. 2, like FIG. 1, shows the system extending from the distal probe 30 to proximal terminals 36C, 40C and 42C.

FIG. 4 shows the distal recess 52 for engaging the nose 54 of the hand piece 32.

DETAILED DESCRIPTION

Figure 1:
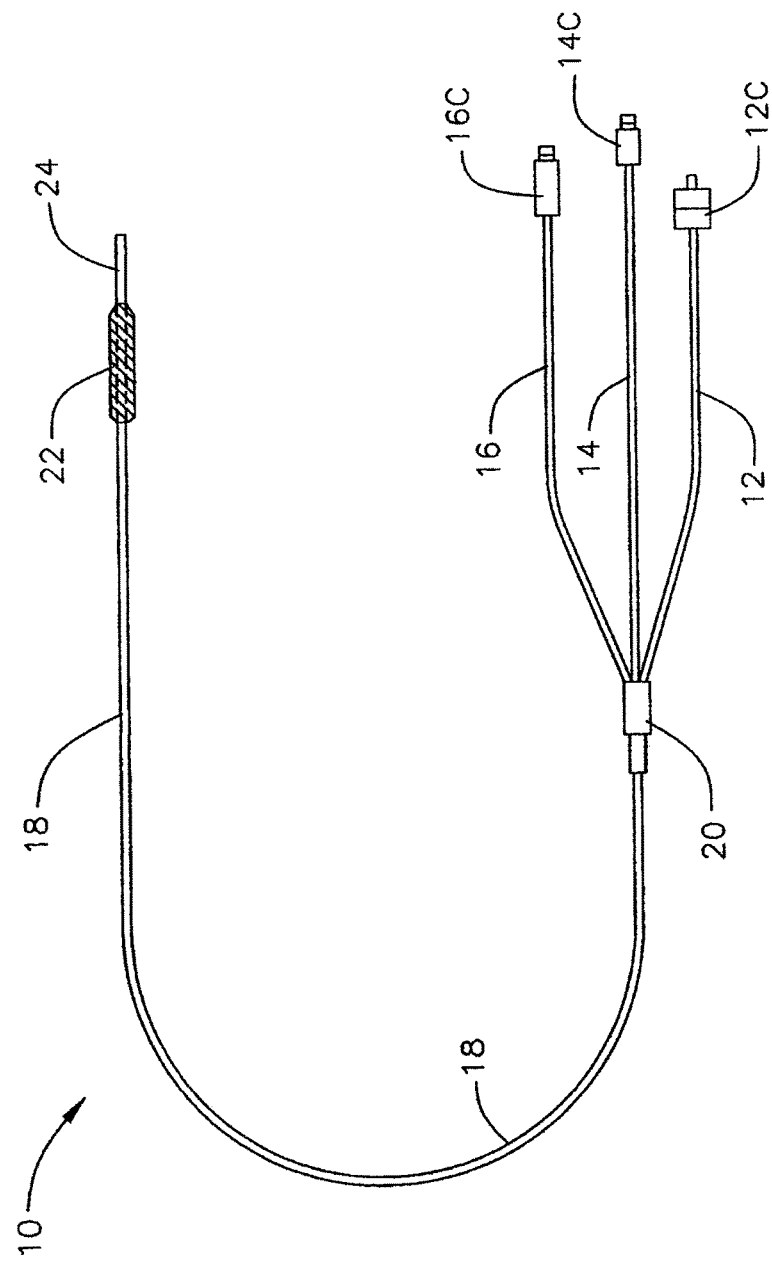
FIG. 1 is a schematic illustration of the prior art system extending from the probe 24 to the terminals 12C, 14C and 16C.

Except for the prior art FIG. 1, the figures are all to a single embodiment.

As shown in FIG. 1, the known laser video endoscopes have an operating probe 24, a hand piece 22, a cable 18 which carries a laser guide 12, an illumination guide 14 and an image guide 16. These are all fiber optic guides which extend from the distal end of the probe 24 to the terminals 12C, 14C and 16C. Distal of the trifurcation zone 20, the fiber optic guides are combined geometrically to provide a minimum diameter cable.

Figure 2:
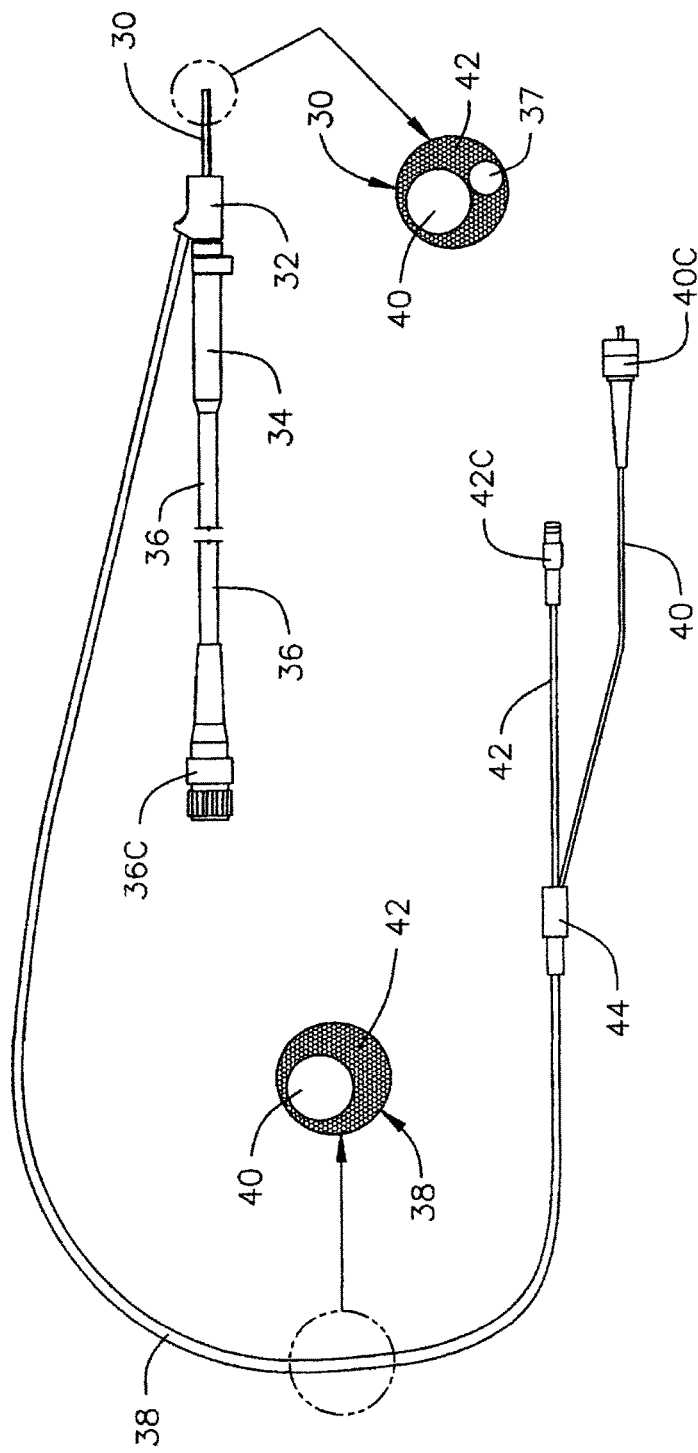
FIG. 2 is a schematic illustration of the embodiment of the invention disclosed herein.
Figure 3:
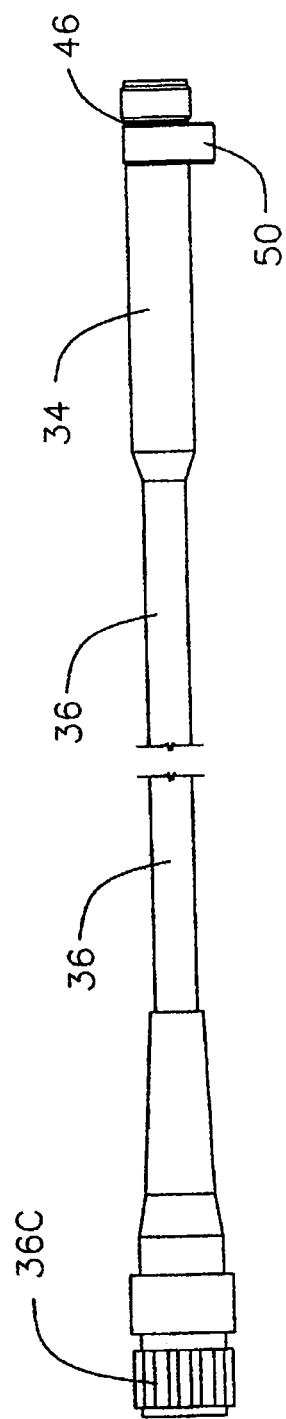
FIG. 3 is a longitudinal view of the camera assembly 34, cable 36 and proximal connector 36C.

As shown in FIG. 2, a laser video endoscope of this invention includes the probe 30, a specifically designed hand piece 32 and a camera assembly 34 coupled to the proximal end of the hand piece 36.

The camera assembly 34 is directly connected to the proximal end of the hand piece 32 through engagement of the nose 54 and recess 52. At the end of the hand piece channel 57, a relatively long electrical cable 36 extends proximally to a terminal 36C which is coupled to an appropriate display mechanism including a video screen so that the operating surgeon can view the image during the course of manipulating the probe.

A optical guide cable 38 extends in the proximal direction from the hand piece 32 to a bifurcation junction 44. This cable 38 carries the laser and illumination guides 40 and 42 for conveying the laser energy and the illumination energy to the probe 30. At the bifurcation junction 44, the laser guide 40 and illumination guide 42 are separated and terminated at the terminals 40C and 42C for connection to the sources of laser energy and illumination energy. The image carrying electrical cable 36 is about as long as is the optical guide cable 38. Each cable 36, 38 can be as long as required for an installation.

As shown by the coupling mechanism in the camera assembly 34, the optical fibers 40 which extend through the probe 30 and hand piece 32 carry the image and are removably coupled to the camera so that the camera provides an electrical image that is transmitted along the electric cable 36 to the terminal 36C at the base where the video displays are provided. The camera may be any one of a number of known type and may be specially designed to fit the geometry of the camera assembly Thus by positioning the camera assembly 34 at the hand piece 32, the lengthy and expensive optical image guide proximal of the hand piece 32 is avoided. The camera assembly 34 can be uncoupled from the hand piece 32 so that the relatively expensive camera assembly can be reused. This combination of reuse of the camera assembly 34 and elimination of an extensive length of expensive fiber optic image guide means that disposability of the probe 30 is economically acceptable even though the hand piece 32 and the laser and illumination guides 40, 42 in the cable 38 are also disposed of after each medical routine.

Figure 5:
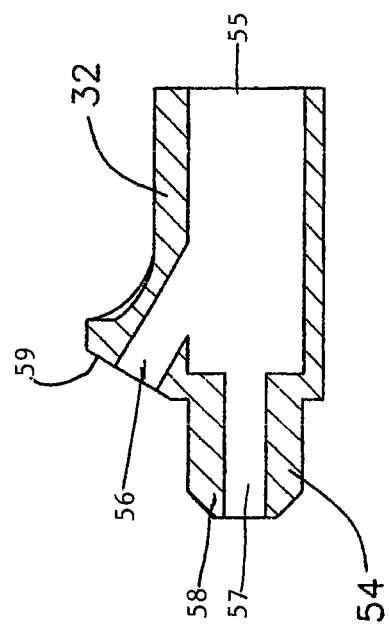
FIG. 5 and FIG. 5A are sectional views of the hand piece 32.
Figure 5A:
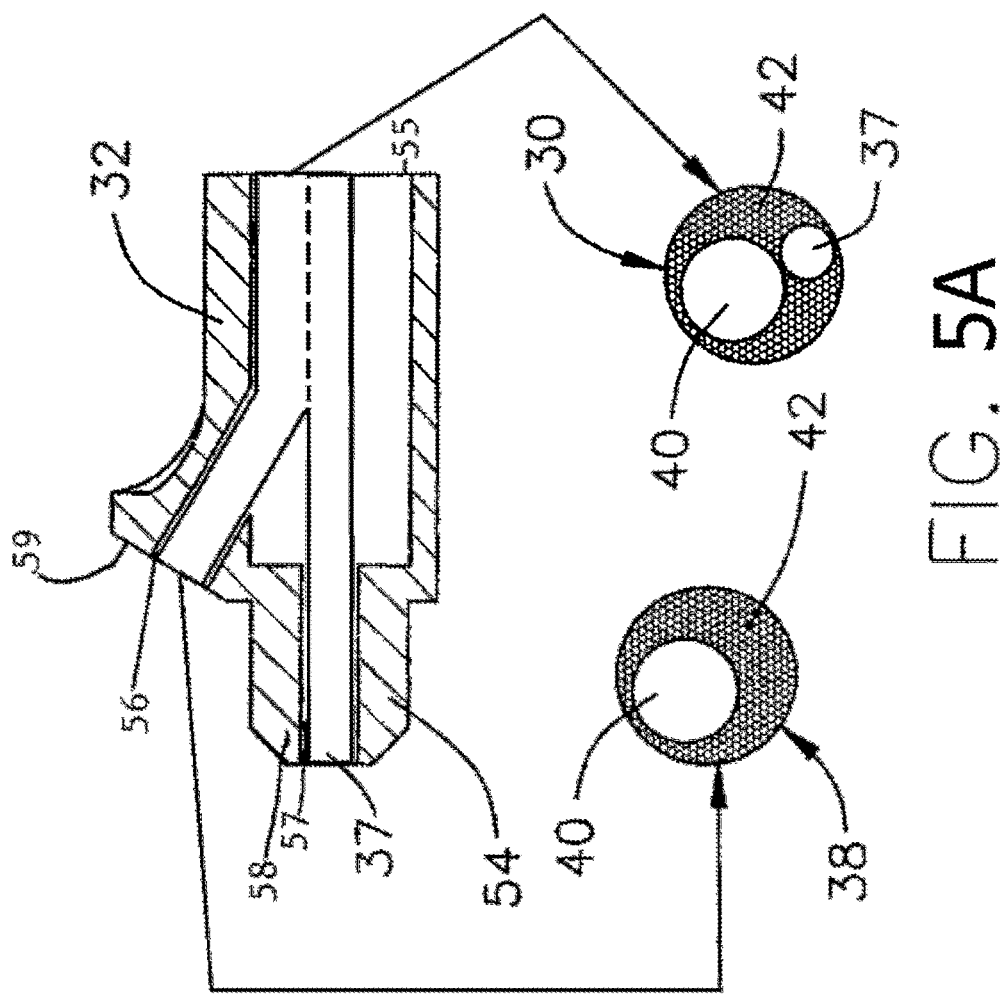

As shown in FIG. 5 and FIG. 5A, the hand piece 32 contains the channels 55, 56 and 57. The channel 57 terminates at hand piece surface 58 and is used to couple the image fibers 37, and only the image fibers, to the lens of the camera assembly 34. The channel 56 terminates at hand piece surface 59 and is used to accommodate the laser fiber 40 and the illumination fibers 42 which are carried proximately by the cable 38. In this fashion, the hand piece 32 separates the image fibers 37 from the illumination 42 and laser 40 fibers. Thus it becomes possible to couple the proximal end of the image fibers 37 to the camera assembly 34 thereby eliminate the costly and lengthy image fibers between hand piece to terminal. The image is carried in an electric cable 36 proximally of the camera assembly 34.

The camera assembly 34 includes a laser filter 46 to protect the camera film from laser energy and to permit the surgeon to observe the operation even when laser pulses are firing. The probe 30 and hand piece 32 are cemented together by a known process.

The camera assembly 34 includes a manually operated spring latch (not shown). The latch is of a known type. It enables readily mounting the camera assembly 34 to the hand piece 32 and, most importantly, removing the camera assembly 34 from the hand piece 32. In addition, the camera assembly 34 includes a focus ring 50 to assure adequate focus of the image provided at the proximal end of the laser fiber image guide 37 in the probe 30 and hand piece 32 onto the image receptors of the camera.

Figure 4:
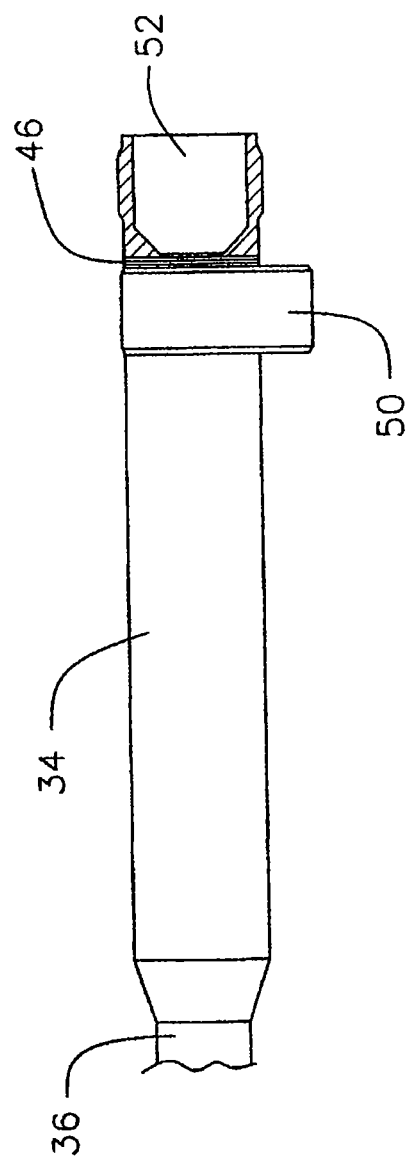
FIG. 4 is a partial longitudinal sectional view of the camera assembly 34 showing camera housing 34, focus ring 50 and laser filter 46.
Figure 6:
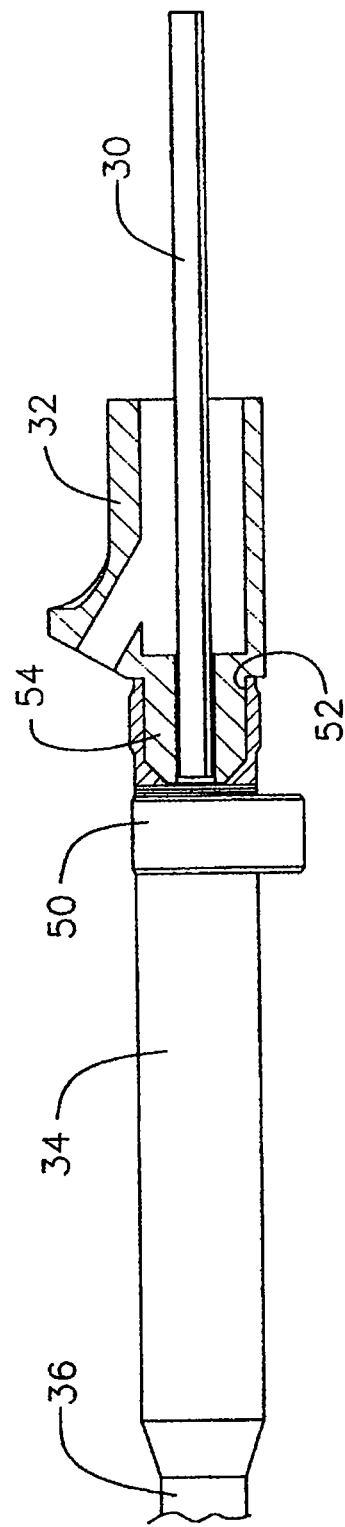
FIG. 6 is a view similar to that of FIGS. 4 and 5 showing the probe 30 and hand piece 32 assembled and coupled to the camera assembly 34.

As may be seen from FIGS. 4, 5 and 6, the distal end of the camera assembly has a recess 52 which engages a nose 54 of the hand piece 32. The latch holds the nose 54 in place in the recess 52.

The image guide 37 in the probe 30 and hand piece 32 costs about $8.00. This reduction in cost from about $200.00 to $8.00 is a major factor encouraging disposable use of the endoscope.

A variant on the illustrated embodiment is an arrangement in which the uncoupling at the proximal end of the hand piece 32 will uncouple not only the camera assembly 34 but also the cable 38 so that only the probe 30 and the hand piece 32 would be disposed of between each operation.

It has to be kept in mind that the positioning of the camera assembly 34 at the hand piece 32 permits a standard optical coupling of the image at the proximal end of the optical fiber image guide 37 to the camera assembly 34. It is not feasible to provide a mechanism that will permit coupling and uncoupling the fiber optic image guide 37 at a junction other than the input to the camera. Coupling and uncoupling is otherwise not feasible because of the enormous number of optical fibers which would have to be aligned for such coupling to provide an image that is not degraded or useless.

While the foregoing description and drawings represent the presently preferred embodiments of the invention, it should be understood that those skilled in the art will be able to make changes and modifications to those embodiments without departing from the teachings of the invention and the scope of the claims.

For example, the image guide 37 within the probe 30 and hand piece 32 is a fiber optic bundle of the type normally used. However, there are other means to provide an image guide. One such is the gradient index lens, often referred to as a GRIN lens.

What is claimed is:

1. A single use surgical endoscope comprising:
   a hand piece having a distal surface and first and second proximal surfaces;
   a laser and illumination first channel in said hand piece extending distally from said first proximal surface;
   an image second channel in said hand piece extending distally from said second proximal surface;
   a laser and illumination and image third channel in said hand piece extending proximally from said distal surface;
   said channels being in communication with each other within said hand piece;
   a rigid probe extending distally from said third channel at said distal surface of said hand piece, said probe containing an illumination guide, a laser guide and an image guide, said illumination, laser and image guides extending into said third channel from a proximal end of said probe and terminating at a distal end of said probe;
   said first channel having a first axis;
   said second channel having a second axis;
   said third channel having a third axis;
   said second and third axes being substantially coaxial, said first axis having a non-zero angle relationship to said second and third axis;
   said illumination guide and said laser guide extending proximally from said probe to said first proximal surface of said hand piece, said laser guide extending further from said first proximal surface to a first proximal end adapted to be connected to a laser source, and said illumination guide extending further from said first proximal surface to a second proximal end adapted to be connected to an illumination source;
   said image guide extending proximally from said probe to said second proximal surface of said hand piece, said image guide having a third proximal end in said second channel at said second proximal surface of said hand piece, said image guide extending through said probe and said hand piece;
   wherein said hand piece is adapted to be detachably mounted to a camera assembly at said second proximal surface to couple said third proximal end of said image guide to said camera assembly,
   whereby when the camera assembly is detached from said hand piece, said first proximal end of said laser guide is detached from said laser source, and said second proximal end of said illumination guide is detached from said illumination sources, said probe, said hand piece, and said illumination, laser and image guides are disposable.

2. The endoscope of claim 1, wherein,
said hand piece includes a proximally extending nose for engaging a camera assembly,
said second channel extending through said nose, and
said second proximal surface constituting the end of said nose.

3. The endoscope of claim 1, wherein said image guide is constituted by optical fibers.

4. The endoscope of claim 1, wherein said illumination guide includes a set of optical fibers that, in said probe, are nested around said laser and image guides to fill the space within said probe.

5. The endoscope of claim 1, wherein said camera assembly comprises a latch adapted to removably mount the camera assembly to the hand piece.

6. The endoscope of claim 1, wherein said camera assembly is directly mounted to the hand piece and an output of the camera assembly is adapted to be coupled to a remote display by an electric cable.

7. The endoscope of claim 1, wherein said rigid probe comprises a steel sidewall extending from said proximal end of said probe and terminating at said distal end of said probe, and containing said illumination guide, said laser guide and said image guide.

\* \* \* \* \*